United States Patent [19]

Knutson et al.

[11] Patent Number: 5,488,120

[45] Date of Patent: Jan. 30, 1996

[54] 1α-HYDROXY VITAMIN $D_4$ AND NOVEL INTERMEDIATES AND ANALOGUES

[75] Inventors: Joyce C. Knutson, Madison; Charles W. Bishop, Verona, both of Wis.; Robert M. Moriarty, Oak Park, Ill.

[73] Assignee: Lunar Corporation, Madison, Wis.

[21] Appl. No.: 296,084

[22] Filed: Aug. 24, 1994

Related U.S. Application Data

[63] Continuation of Ser. No. 991,493, Dec. 17, 1992, abandoned, which is a continuation of Ser. No. 800,045, Nov. 29, 1991, abandoned, which is a continuation of Ser. No. 586,854, Sep. 21, 1990, abandoned.

[51] Int. Cl.[6] .................................................. C07C 401/00
[52] U.S. Cl. ............................................................. 552/653
[58] Field of Search ............................................. 552/653

[56] References Cited

U.S. PATENT DOCUMENTS

| | | |
|---|---|---|
| 2,383,446 | 6/1941 | Calcott et al. . |
| 4,195,027 | 3/1980 | DeLuca et al. . |
| 4,202,829 | 5/1980 | DeLuca et al. . |
| 4,260,549 | 4/1981 | DeLuca et al. ........................ 552/653 |
| 4,362,710 | 12/1982 | Watanabe . |
| 4,661,294 | 4/1987 | Holick et al. ........................ 260/397.2 |
| 4,866,048 | 9/1989 | Calverley et al. ...................... 552/653 |
| 5,157,135 | 10/1992 | Tsuji et al. .............................. 552/653 |

OTHER PUBLICATIONS

Harrison's Principals of Internal Medicine: Part Eleven, "Disorders of Bone and Mineral Metabolism" Chap. 335, in E. Braunwald, K. J. Isselbacher, R. G. Petersdorf, J. D. Wilson, J. B. Martin and H. S. Fauci (eds.), *Calcium, Phosphorous and Bone Metabolism: Calcium Regulating Hormones*, McGraw–Hill, New York, pp. 1860–1865 (1984).

DeLuca, H. F., Weller, M., et al., *Arch Biochem. and Biophys.*, 124: 122–128 (1968).

*Merck Index*, S. Budavari (ed.), 11th ed., Merck & Lo., Rathway, N.J., (1989) pp. 1579, #930.

McDonald, F. G., *J. Biol. Chem.*, 114:lxv (1936).

Tsuji et al., "Synthesis of 22,23–Dihydro–1α, 25–dihydroxyvitamin $D_2$ and Its 24R–Epimer, New Vitamin $D_2$ Derivatives", *Bull. Chem. Soc. Jpn.*, 63, 2233–2238, Aug. 1990.

DeLuca, et al., "Synthesis, Biological Activity, and Metabolism of 22,23-$^3$H Vitamin D4," Arch. Biochem. Biophys. 124, pp. 122–128 (1968).

*Primary Examiner*—Johann Richter
*Assistant Examiner*—Kimberly J. Kestler
*Attorney, Agent, or Firm*—Stroud, Stroud, Willink, Thompson & Howard

[57] ABSTRACT

Novel 1α-hydroxy Vitamin $D_4$ and novel analogues, 1,25 dihydroxy Vitamin $D_4$ and 1,24 dihydroxy Vitamin $D_4$ which are useful for the treatment of disorders of calcium metabolism. Preparation of the novel 1α-hydroxy Vitamin $D_4$ starts from ergosterol which is converted in six steps to 22,23-dihydroergosterol. 22,23-dihydroergosterol was irradiated to yield Vitamin $D_4$ which was converted in four steps to 1α-hydroxy Vitamin $D_4$ using a cyclovitamin procedure which produced the novel intermediates, Vitamin $D_4$ tosylate, 3,5 cyclovitamin $D_4$ and 1α-hydroxy cyclovitamin $D_4$. 1,25 dihydroxy Vitamin $D_4$ and 1,24 dihydroxy Vitamin $D_4$ are isolated as biological products of the metabolism of novel 1α-hydroxy Vitamin $D_4$ using cultured human liver cells.

1 Claim, 2 Drawing Sheets

1α-HYDROXY VITAMIN D₄ AND NOVEL INTERMEDIATES AND ANALOGUES

This is a continuation of application Ser. No. 07/991,493 filed Dec. 17, 1992, now abandoned, which is a continuation of application Ser. No. 07/800,045, filed Nov. 29, 1991, now abandoned, which is a continuation of application Ser. No. 07/586,854, filed Sep. 21, 1990, now abandoned.

TECHNICAL FIELD

This invention relates to biologically active Vitamin $D_4$ compounds. More specifically, this invention relates to novel 1α-hydroxy Vitamin $D_4$ and novel intermediates used in its synthesis, novel 1,25 dihydroxy Vitamin $D_4$ and novel 1,24 dihydroxy Vitamin $D_4$.

BACKGROUND

Vitamin D is known to be important in the regulation of calcium metabolism in animals and man. See, Harrison's Principals of Internal Medicine: Part Eleven, "Disorders of Bone and Mineral Metabolism, Chapter 335," in E. Braunwald, K. J. Isselbacher, R. G. Petersdorf, J. D. Wilson, J. B. Martin and A. S. Fauci (eds.), *Calcium, Phosphorous, and Bone Metabolism: Calcium Regulating Hormones*, McGraw-Hill, New York, 1987, pp. 1860–1865. The two most commonly known, useful forms of Vitamin D are Vitamin $D_3$ and Vitamin $D_2$. Vitamin $D_3$ is synthesized endogenously in the skin of animals and man, whereas Vitamin $D_2$ is the form of Vitamin D supplied by plants. Vitamin $D_2$ differs from Vitamin $D_3$ in that it contains a double bond between C22 and C23 and further contains a C24-methyl group. In man and rats, Vitamin $D_3$ and Vitamin $D_2$ have equivalent biopotency.

Vitamin $D_4$, also known as irradiated 22-dihydroergosterol or 22,23-dihydro Vitamin $D_2$ or 22,23-dihydroergocalciferol, differs from Vitamin $D_3$ in that it contains a C24 methyl group. Vitamin $D_4$ was first described in 1936. Grab, W., *Z. Physiol. Chem.*, 243:63 (1936); McDonald, F. G., *J. Biol. Chem.*, 114:IVX (1936). See also Windhaus, A. and Trautmann, G., *Z. Physiol. Chem.*, 247:185–188 (1937). These references report some disagreement as to the level of biological activity of the Vitamin suggesting that in the rat, Vitamin $D_4$ is one-third or three-fourths as active as Vitamin $D_3$ and in the chick, either one-tenth or one-fifth as active as Vitamin $D_3$.

A more definitive study of the biological activity of Vitamin $D_4$ was made by DeLuca, et. al., in 1968. DeLuca, H. F., Weller, M., Blunt, J. W. and Neville, P. F., *Arch. Biochem. Biophys.*, 124:122–128 (1968). There, the authors confirmed that Vitamin $D_4$ was less active than Vitamin $D_3$. DeLuca, et. al., reports that in their hands Vitamin $D_4$ is two-thirds as active as Vitamin $D_3$ or Vitamin $D_2$ in the rat, and one-fifth as active as Vitamin $D_3$ in the chick.

DeLuca, et. al., make reference to the fact that "[t] the synthesis of Vitamin $D_4$ has apparently been little used since it was first described by Windhaus and Trautmann," and comment, "this is perhaps due to the fact that Vitamin $D_4$ is only of academic interest."

To applicants' knowledge, Vitamin $D_4$ has remained "only of academic interest" as applicants are unaware of any further study of Vitamin $D_4$ since that reported by DeLuca, et. al. In fact, *The Merck Index* states with respect to Vitamin $D_4$, "Its biological activity seems doubtful." "Merck Index," S. Budavari (ed.), 11th ed., Merck & Co., Rathway, N.J., 1989, pp. 1579, #9930.

Since DeLuca, et. al., discovered the active form of Vitamin $D_3$, 1,25-dihydroxy Vitamin $D_3$, (U.S. Pat. No. 3,697,559) and its synthetic precursor, 1α-hydroxy Vitamin $D_3$, (U.S. Pat. No. 3,741,996) most interest has centered on developing therapeutic uses of these active Vitamin $D_3$ metabolites. Unfortunately, while the Vitamin $D_3$ metabolites held great promise as therapeutic agents, this promise has never been fully realized because of the extreme toxicity of these agents. What is needed is a biopotent Vitamin D metabolite of low toxicity such that the drug is practical as a therapeutic agent.

SUMMARY OF THE INVENTION

The novel compounds of the invention 1α-hydroxy Vitamin $D_4$, 1,25-dihydroxy Vitamin $D_4$ and 1,24-dihydroxy Vitamin $D_4$, are bioactive forms of Vitamin $D_4$. The present inventors have discovered that these active forms of Vitamin $D_4$ display much greater biopotency than would be predicted on the basis of the previously reported bioassays of Vitamin $D_4$. The present inventors have also discovered, that the bioactive novel compounds are less toxic than would be predicted on the basis of their biopotency. This combination of high activity with low toxicity makes the compounds of the invention useful as therapeutic agents in the treatment of disorders of calcium metabolism.

In order to study the novel compounds of the invention, it was necessary to develop processes for their production. One alpha-hydroxy vitamin $D_4$ was made synthetically and in the course of that synthesis novel intermediates were also produced. 1,25-dihydroxy Vitamin $D_4$ and 1,24-dihydroxy Vitamin $D_4$ are isolated as biological products of the metabolism of 1α-hydroxy Vitamin $D_4$. The following disclosure describes the novel compounds and the processes for their production.

The biologically active compounds of the present invention have the following general formula (I):

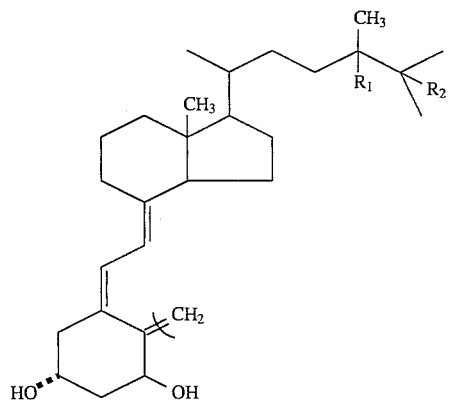

wherein:

$R_1$ is either H or OH, and $R_2$ is either H or OH but $R_1$ and $R_2$ cannot both has OH.

Example 1: Synthesis of 1α-hydroxy Vitamin $D_4$

Figure 1:
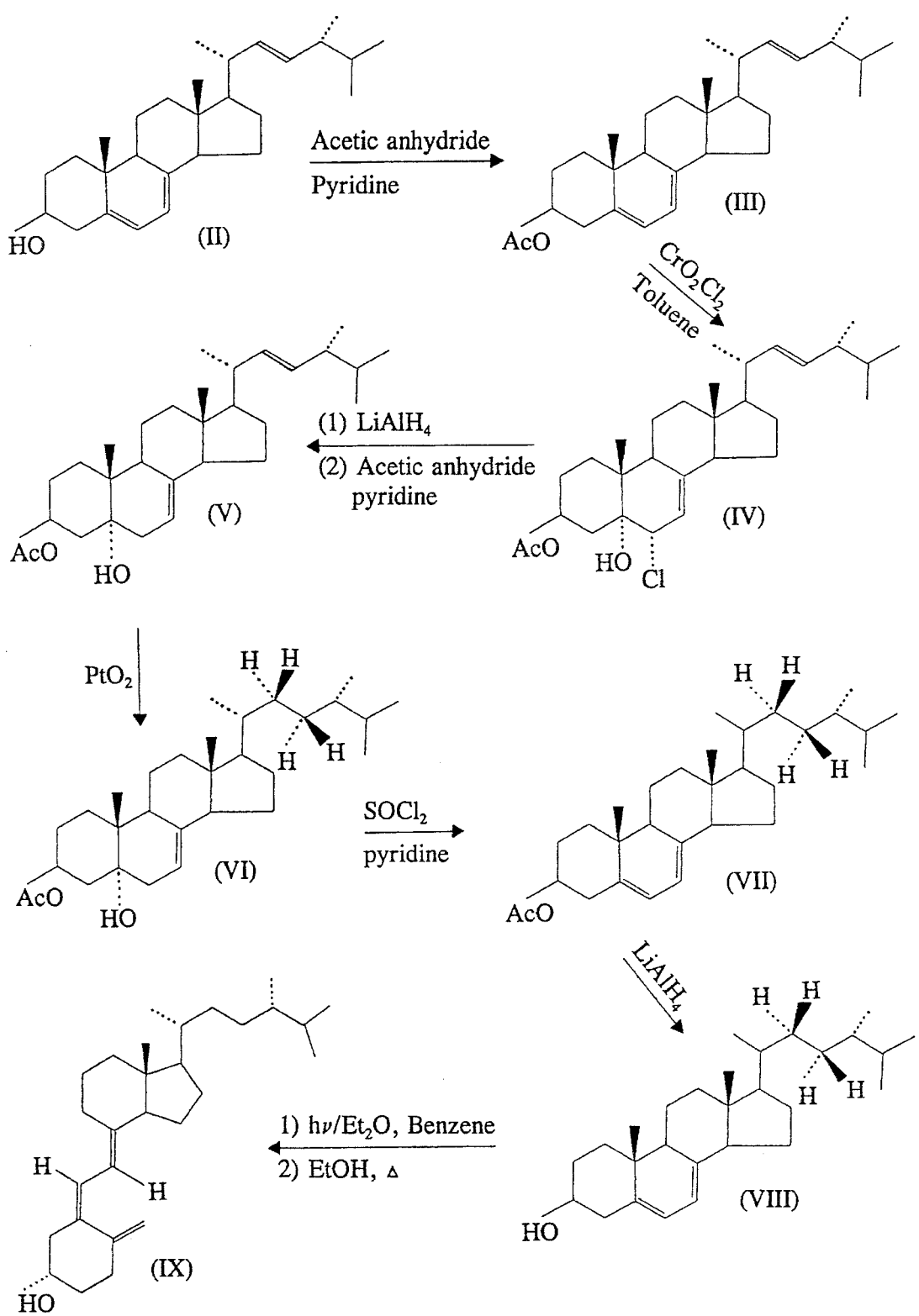
FIG. 1 depicts the synthesis of vitamin $D_4$ from ergosterol.
Figure 2:
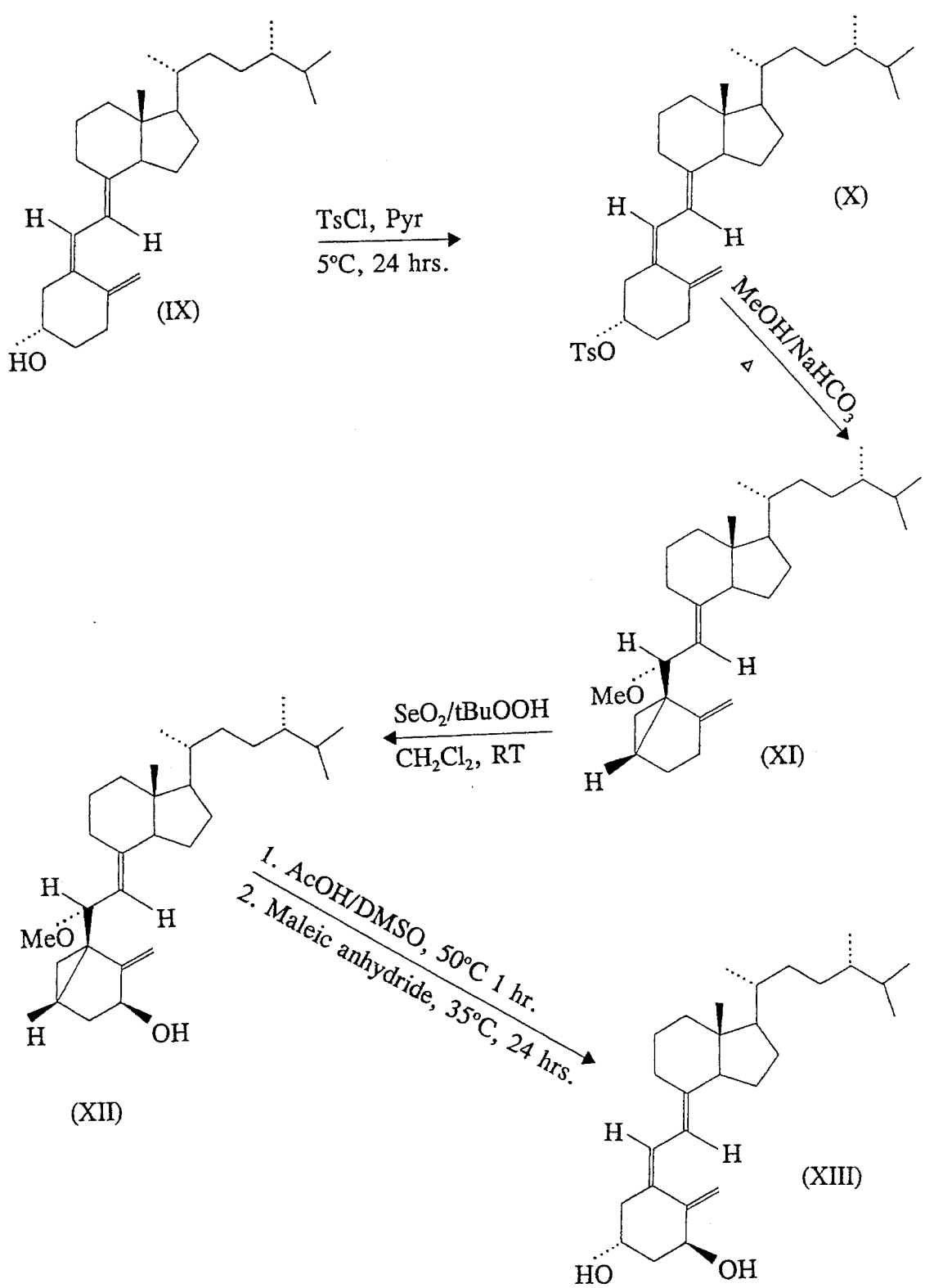
FIG. 2 depicts the synthesis of 1α-hydroxy vitamin $D_4$ from vitamin $D_4$.

Synthesis of 1α-hydroxy Vitamin $D_4$ was accomplished according to the plan presented in the schema of FIGS. 1 and 2. The synthesis began with ergosterol as the starting material which was converted in six steps to 22,23-dihydroergosterol (VIII) according to the procedure of Barton, et. al., *JCS Perkin I*, 1976, 821–826. 22,23-dihydroergosterol was then irradiated as described in Windhaus, et. al., *Z. Physiol. Chem.*, 1937, 147:185, to yield Vitamin $D_4$ [22,23-dihydroergocalciferol] (IX). See, FIG. 1. Vitamin $D_4$ was then converted in four steps to 1α-hydroxy Vitamin $D_4$ using a procedure analogous to that described by Paaren, et. al., *J. Org. Chem.*, 1980, 45:3253.

Detailed Procedure of Synthesis of 1α-hydroxy Vitamin $D_4$

Ergosterol (II) was converted to ergosterol acetate (III) by dissolving 100 g. (0.25 mol.) ergosterol in 600 ml. of anhydrous pyridine and 68 ml. (0.7 mol.) acetic anhydride. The solution was stirred overnight at room temperature after which time the solution was cooled by adding 1.2L. ice, causing a precipitate to form. The precipitate was washed five times with 400 ml. portions of water, then once with 400 ml. of $CH_3CN$. The resulting product was air dried to yield 79 g. (71%) of ergosterol acetate as a white crystalline solid. m.p.: 169°–171° C.; $^1H$ NMR: (400 MHz, $CDCl_3$), δppm 2.05 (3H, s, 3β-$CH_3CO$), 4.65~4.75 (1H, m, 3α-H) 5.15~5.25 (2H, m, 22-H and 23-H), 5.4 (1H, d, 6-H), 5.6 (1H, d, 7-H) FTIR [KBr] 1734 $cm^{-1}$ (C=O stretching) 968 $cm^{-1}$ (C-H bending).

Ergosterol acetate (III) was dissolved in 2.5L. freshly distilled deoxygenated toluene. To this solution 9 ml. (0.111 mol.) chromyl chloride dissolved in 240 ml. dry $CH_2CL_2$ was added under nitrogen at −78° C. over a thirty minute period. The reaction system was stirred at −78° C. for an additional fifteen minutes and then 62 ml. of a saturated solution of sodium borohydride in ethanol was added in one portion. After stirring at −78° C. for an additional fifteen minutes, the reaction solution was poured into a two phase system of 3N hydrochloric acid (3L.) and benzene (3L.). The organic layer was separated, then washed with water (2L.), twice with a brine solution (2×1L.) and then dried with anhydrous $MgSO_4$. The dried solution was filtered and concentrated in vacuo. The crude crystalline product was then treated with $CH_3CN$ (280ml.) and filtration of the thus formed slurry yielded 12.5g. (41%) of white crystalline 3β-Acetoxy-6α-chloroergosta-7,22-dien-5α-ol (IV). m.p.: 190°–192° C.; $^1H$ NMR: (400 MHz, $CDCl_3$), βppm 2.05 (3H, s, 3β-OAc), 4.65 (1H, d, 6β-H), 5.1 (1H, s, 7-H), 5.1$^{-5.3}$ (2H, m, 22-H and 23-H), FTIR [KBr] 1732 $cm^{-1}$ (C=O stretching), 968 $cm^{-1}$ (C-H bending), 3437 $cm^{-1}$ (O-H stretching).

The 3β-Acetoxy 6α-chloroergosta-7,22-dien-5α-ol (IV) (21.4 g., 0.044 mol.) in dry THF (900 ml.) was added slowly to a stirred suspension of lithium aluminium hydride (2.66 g., 0.07 mol.) in dry THF (750 ml.) at room temperature under nitrogen. The mixture was refluxed for three hours and cooled to 0° C. Excess hydride was decomposed with saturated $Na_2SO_4$ solution. Filtration through anhydrous Na $_2SO_4$ and evaporation of the filtrate gave a solid, which was treated directly with acetic anhydride (110 ml.) and dry pyridine (220 ml.) at 0° C. Removal of solvent under reduced pressure yielded the acetate (12.75 g., 61%), 3β-Acetoxyergosta-7,22-dien-5α-ol (V). m.p.: 229°–232° C.; FTIR [KBr] 1736 $cm^{-1}$ (C=O stretching), 3460 $cm^{-1}$ (O-H stretching), 972 $cm^{-1}$ (C-H bending).

3β-Acetoxyergosta-7,22-dien-5α-ol (V) (2.5 g., 0.0055 mol.) was shaken for sixteen hours with freshly prepared $PtO_2$ (0.5 g.) in ethyl acetate (820 ml.) under $H_2$ gas (15 lbs/sq. in.). The catalyst was removed by filtration and evaporation of the filtrate gave the crude acetate which was dissolved in $CH_2CL_2$ and chromatographed on silica gel. Elution with $CH_2Cl_2$ gave substantially pure 3β-Acetoxyergost-7-en-5α-ol (VI) (2.15 g., 85%) as a white crystalline material. m.p.: 228°–232° C.; $^1H$ NMR: (400 MHz, $CDCl_3$), δppm 2.05 (3H, s, 3β-OAc), 5.05~5.20 (2H, m, 3α-H and 7-H) FTIR [KBr] 1736 $cm^{-1}$ (C=O stretching), 3462 $cm^{-1}$ (O-H stretching).

Redistilled thionyl chloride (9.7 ml.) in dry pyridine (170 ml.) was added to compound 3β-Acetoxyergost-7-en-5α-ol (VI) (12.0 g., 0.0262 mol.) in dry pyridine (800 ml.) at 0° C. under nitrogen. After 2.5 hours, the solution was diluted with ice cold $H_2O$ (1.5 L.) and extracted with two portions of ether (2.5 L.+ 1.5 L.). The combined ether extracts were washed with a $NaHCO_3$ solution (1.0 L.×2), then 1N HCl (1.5 L.×2) and then water (1 L.). The ether solution was dried with $MgSO_4$, and after filtration, evaporated under reduced pressure to yield a crude product which was converted to a slurry with $CH_3CN$ (100 ml.). The product was collected by filtration and recrystallized from $CH_3CN$ to yield 4.5 g. (39%) of a white crystalline 22,23-dihydroergosteryl acetate (VII). m.p.: 144°–147° C.; $^1H$ NMR: (400 MHz, $CDCl_3$), δppm 2.05 (3H, s, 3β-OAc), 4.65~4.75 (1H, m, 3α-H), 5.4 (1H, d, 6-H), 5.6 (1H, d, 7-H) FTIR [KBr] 1734 $cm^{-1}$ (C=O stretching).

Compound 22,23-dihydroergosteryl acetate (VII) (4.8 g., 0.011 mol.) was added at once to a stirred suspension of lithium aluminium hydride (2.5 g., 0.066 mol.) in dry ether (1.1 L.) at room temperature. The mixture was stirred for two hours at room temperature. 5N NaOH was added to destroy excess lithium aluminium hydride and $H_2O$ (500 ml.) was then added. The aqueous solution was then extracted with four 250 ml. portions of ether. The combined ether extracts and combined organic layer were washed with brine solution (1 L.), then dried with $Na_2SO_4$. Evaporation of ether under reduced pressure gave the compound, 22,23-dihydroergosterol, (VIII) (4.1 g., 94%) as a white crystalline material. m.p.: 147°–150° C.; $^1H$ NMR: (400 MHz, $CDCl_3$), δppm 3.6~3.7 (1H, m, 3α-H), 5.4 (1H, d, 6H), 5.6 (1H, d, 7-H) FTIR [KBr] 3400 $cm^{-1}$ (O-H stretching).

22,23-dihydroergosterol (VIII) (2.0 g., 5.0 mmol.) was dissolved in a solution of diethyl ether and benzene (4:1, 600 ml.) and irradiated (Hannovia immersion lamp 450 watts) with stirring under argon in a water cooled quartz vessel for three hours. The solution was concentrated in vacuo to yield a gummy liquid, redissolved in 100 ml. of ethanol and heated at reflux under argon for eight hours. Then, the solution was concentrated in vacuo and the residue was adsorbed on a silica gel column and eluted with 30% ethyl acetate in hexane to afford Vitamin $D_4$ (22,23-dihydroergocalciferol) (IX). 1.2 g. (60%). $^1H$ NMR: (400 MHz, $CDCl_3$), δppm 0.55 (3H, s, 18-$H_3$) 0.78 (6H, dd, 26-$H_3$ and 27-$H_3$) 0.87 (3H, d, 21-$H_3$) 0.93 (3H, d, 28-$H_3$) 3.94 (1H, m, 3-H) 4.82 (1H, m (sharp), 19-H), 5.04 (1H, m (sharp), 19-H), 6.04 (1H, d, 7-H) 6.24 (1H, d, 6-H).

To a stirred solution of Vitamin $D_4$ (IX) (3.0 g., 7.5 mmol.) in 10 ml. of dry pyridine was added freshly recrystallized p-toluenesulfonyl chloride (3.6 g., 19 mmol.) at 0° C. The reaction mixture was stirred at 5° C. or 24 hours and was then quenched by pouring the mixture over ice and saturated $NaHCO_3$ (100 ml.) with stirring. The aqueous suspension was extracted with $CH_2Cl_2$ (3×300 ml.). The combined organic extracts were washed with 10% HCl (3×200 ml.), saturated $NaHCO_3$ (3×200 ml.) and saturated NaCl (2×200 ml.) , dried over $MgSO_4$ and concentrated in vacuo to yield 3.5 g. (84%) of the novel intermediate compound Vitamin $D_4$ tosylate (X). $^1H$ NMR (400 MHz, $CDCl_3$), δppm 0.54 (3H, s, 18-$H_3$) 0.78 (6H, dd, 26-$H_3$ and 27-$H_3$) 0.87 (3H, d, 21-$H_3$), 0.96 (3H, d, 28-$H_3$) 2.45 (3H, s, $CH_3$ (tosylate) 4.68 (3H, m, 3-H) 4.82 (1H, m (sharp), 19-H) 5.04 (1H, m (sharp), 19-H), 5.95 (1H, d 7-H), 6.09 (1H, d, 6-H) 7.34 and 7.79 (4H, d, aromatic).

To a stirred suspension of $NaHCO_3$ (17.0 g., 202 mmol.) in methanol (200 ml.) was added dropwise to a solution of Vitamin $D_4$ tosylate (X) (3.5. g., 6.3 mmol.) in dry $CH_2Cl_2$ (10 ml.). The reaction mixture was refluxed overnight under argon. Cooled to room temperature and concentrated in vacuo to about 50 ml. The reaction concentrate was diluted with ether (600 ml.), washed with water (3×300 ml.), dried over $MgSO_4$ and concentrated in vacuo and the residue was passed through a silica gel column and eluted with 10% ethyl acetate in hexane to afford the novel intermediate compound 3,5 cyclovitamin $D_4$ (XI) (heavy oil) 1.5 g. (58%). $^1H$ NMR (400 MHz, $CDCl_3$), δppm 0.56 (3H, s, 18-$H_3$) 0.78 (6H, dd, 26-$H_3$ and 27-$H_3$), 0.87 (3H, d, 21-$H_3$), 0.94 (3H, d, 28-$H_3$), 3.28 (3H, s, $OCH_3$) 4.2 (1H, d, 6-H), 4.91 (1H, m (sharp), 19-H), 4.98 (1H, d 7-H), 5.08 (1H, m (sharp), 19-H).

Anhydrous tert-butyl hydroperoxide in toluene (3M) (2.6 ml., 7.8 mmol.) was added to a stirred suspension of selenium dioxide (0.22 g., 2 mmol.) in dry $CH_2Cl_2$ (150 ml.) in a three necked flask. The mixture was stirred for three hours under argon. Pyridine (0.3 ml., 3.7 mmol.) was then added and then cyclovitamin $D_4$ (XI) (1.5 g., 3.6 mmol.) was introduced as a solution in $CH_2Cl_2$ (50 ml.). After stirring for thirty minutes, 10% aqueous NaOH solution (200 ml.) was added and then the reaction mixture was diluted with ether (500 ml) and the phases were separated. The organic phase was washed with 10% NaOH (3×200 ml.), water (2×200 ml.) and saturated NaCl solution (2×200 ml.), dried over $MgSO_4$ and concentrated in vacuo. The residue was absorbed on a silica gel column and eluted with 30% ethyl acetate in hexane to afford 0.45 g. (29%) of the novel intermediate compound 1α-hydroxy 3,5-cyclovitamin $D_4$ (XII) (oil). $^1H$ NMR (400 MHz, $CDCl_3$), δppm 0.54 (3H, s, 18-$H_3$) 0.78 (6H, dd, 26-$H_3$ and 27-$H_3$) 0.86 (3H, d, 21-$H_3$) 0.95 (3H, d, 28-$H_3$) 3.26 (3H, s, $OCH_3$) 4.2 (1H, d, 6-H), 4.22 (1H, m, 1-H), 4.95 (1H, d 7-H), 5.18 (1H, d, 19-H) 5.25 (1H, d, 19-H).

A solution of 1α-hydroxy 3,5-cyclovitamin $D_4$ (XII) (0.45 g., 1.05 mmol.) in a solution of dimethyl sulfoxide (4.5 ml.) and glacial acetic acid (3.6 ml.) was heated to 50° C. under argon for one hour. The reaction mixture was then poured over ice and saturated $NaHCO_3$ solution (100 ml.) and extracted with ether (3×200 ml.). The combined ether extracts were washed with saturated $NaHCO_3$ solution (3×200ml.), water (3×200 ml.) and saturated NaCl solution (3×200 ml.), dried over $MgSO_4$, concentrated in vacuo to give a mixture containing 5,6-cis and 5,6-trans 1α-hydroxy Vitamin $D_4$ (about 4:1 by $^1H$ NMR), 0.4g, (92%). The mixture of 5,6-cis and 5,6-trans 1α-hydroxy Vitamin $D_4$ (0.4 g., 0.97 mmol.) was dissolved in ethyl acetate (25 ml.) and treated with freshly recrystallized maleic anhydride (0.08 g., 0.8 mmol.). This reaction mixture was heated to 35° C. under argon for 24 hours. After evaporation of the solvent in vacuo, the crude mixture was chromatographed over a silica gel column using ethyl acetate and hexane (1:1) as eluent, to afford the novel active form of Vitamin $D_4$, 5,6-cis 1α-hydroxy Vitamin $D_4$ (XIII) 90 mg. (23%). m.p.: 128°–130° C. IR $v_{max}$ (Neat) 3400 $cm^{-1}$ (OH stretching). $^1H$ NMR (400 MHz, $CDCl_3$), δppm 0.55 (3H, s, 18-H) 0.79 (6H, dd, 26-$H_3$ and 27-$H_3$) 0.87 (3H, d, 21-$H_3$) 0.94 (3H, d, 28-$H_3$), 4.24 (1H, m, 3-H), 4.44 (1H, m, 1-H), 5.02 (1H, m (sharp), 19-H), 5.34 (1H, m (sharp), 19-H), 6.02 (1H, d 7-H), 6.4 (1H, d, 6-H). Mass spectrum [CI] m/e (relative intensity) 415 (M+1, 41%) 397, (M+1-OH 100%), 379 (27%), 135 (22%).

Biological testing of 1α-hydroxy Vitamin $D_4$

Male weaning rats were fed a Vitamin D deficient diet containing normal Ca (0.47%) and P (0.3%). After four weeks on this diet the rats had serum calcium values less than 7 mg/dl. The rats were then separated into four groups and orally administered either 1α-hydroxy Vitamin $D_4$ or the vehicle for each of 14 days. Twenty-four hours after the last dose, the rats were killed and the blood calcium measured by a standard laboratory technique.

The results of these determinations are shown in Table 1.

TABLE 1

| | Increase in serum calcium concentration | | |
|---|---|---|---|
| Compound | Dose (mcg/kg/day) | Number of rats | Serum calcium concentration (mg/100 ml) ± Standard Deviation |
| Vehicle | – | 10 | 6.1 ± 0.48 |
| 1α-OH-$D_4$ | 0.042 | 8 | 7.1 ± 0.80 |
| 1α-OH-$D_4$ | 0.250 | 7 | 11.6 ± 0.45 |
| 1α-OH-$D_4$ | 1.500 | 9 | 12.7 ± 0.37 |

The data of table 1 indicate that 1α-hydroxy Vitamin $D_4$ is effective at increasing serum calcium in the Vitamin D deficient rat and that the response appears to be dose dependent. Surprisingly, the level of the response appears to compare favorably to that reported by Wientroub, et. al., for 1,25 dihydroxy Vitamin $D_3$ administered to Vitamin D deficient rats under experimental conditions similar to those described above. See, Wientroub, S., Price, P. A., Reddi, A. H., "The Dichotomy in the Effects of 1,25 dihydroxy Vitamin $D_3$ and 24,25 dihydroxy Vitamin $D_3$ on Bone GammaCarboxyglutamic Acid-Containing Protein in Serum and Bone in Vitamin D-Deficient Rats," *Calcif. Tissue Int.* (1987) 40:166–172.

The acute oral toxicity of 1α-OH-$D_4$ in rats was assessed by determining the mean lethal dose ($LD_{50}$). Rats were fed a standard laboratory diet for 8–10 weeks. Five animals of each sex were administered one oral dose of 1α-OH-$D_4$. The animals were observed for 14 days, and the number of deaths noted. The $LD_{50}$ value was determined to be about 1.0 mg/kg in males and 3.0 mg/kg in females.

For comparison, the $LD_{50}$ value for 1α-hydroxy Vitamin $D_2$ under the same conditions was found by applicant's to be 1.7 and 1.8 mg./kg. in male and female rats, respectively. The toxicity of 1α-hydroxy Vitamin $D_2$ has previously been reported as less than 1α-hydroxy Vitamin $D_3$. Sjoden, G., Smith, C., Lindgren, U., and DeLuca, H. F., *Proc. Soc. Experimental Biol. Med.*, 178:432–436 (1985).

Example 2: Generation and Isolation of 1,25-dihydroxy Vitamin $D_4$

The experimental drug 1α-hydroxy Vitamin $D_4$ is incubated with cultured human liver cells which metabolize the compound to several products including the metabolite 1,25 dihydroxy Vitamin $D_4$. The 1,25 metabolite is isolated and purified by high pressure liquid chromatography and identified by gas-chromatography-mass spectrometry. Binding studies demonstrate that the 1,25 dihydroxy Vitamin $D_4$ has good binding affinity for the mammalian Vitamin D receptor protein indicating it is biologically active. The procedures used are similar to that described by Strugnell, et. al., *Biochem. Pharm. Vol.* 40:333–341 (1990).

Example 3: Generation and isolation of 1,24 dihydroxy Vitamin $D_4$.

Generation and isolation of 1,24 dihydroxy Vitamin $D_4$ is accomplished as described in Example 2, above. The experimental drug 1α-hydroxy Vitamin $D_4$ is incubated with cultured human liver cells which metabolize the compound to several products including the metabolite 1,24 dihydroxy Vitamin $D_4$. The 1,24 metabolite is isolated and purified using high pressure liquid chromatography and identified by gas-chromatography-mass spectrometry. Binding studies with the new metabolite demonstrate that the metabolite has good binding affinity for the mammalian Vitamin D receptor protein which indicates the drug is biologically active.

What we claim is:

1. 1α-hydroxy Vitamin $D_4$.

* * * * *

UNITED STATES PATENT AND TRADEMARK OFFICE
CERTIFICATE OF CORRECTION

PATENT NO. : 5,488,120
DATED : January 30, 1996
INVENTOR(S) : Joyce C. Knutson et al.

It is certified that error appears in the above-indentified patent and that said Letters Patent is hereby corrected as shown below:

Column 2, formula (I), that portion of the formula reading

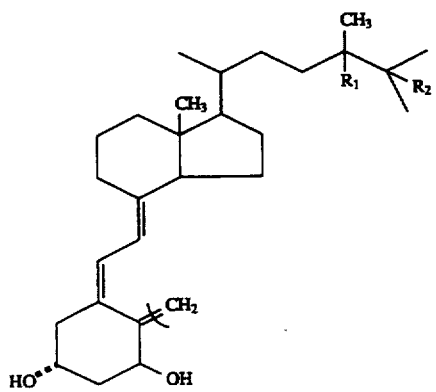

should read

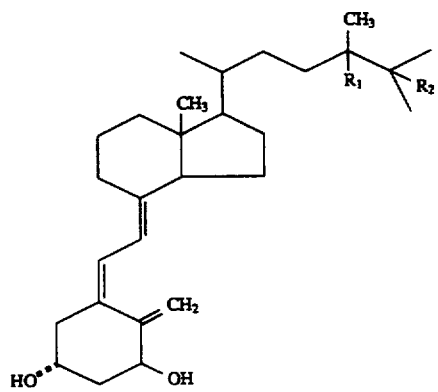

Signed and Sealed this

Twenty-first Day of January, 1997

Bruce Lehman

BRUCE LEHMAN

*Attest:*

*Attesting Officer*  Commissioner of Patents and Trademarks